(12) United States Patent
Ortiz et al.

(10) Patent No.: US 9,480,590 B2
(45) Date of Patent: Nov. 1, 2016

(54) DEVICE FOR ANCHORING AN ENDOLUMINAL SLEEVE IN THE GI TRACT

(75) Inventors: Mark S. Ortiz, Milford, OH (US);
Mark S. Zeiner, Mason, OH (US);
Jason L. Harris, Lebanon, OH (US);
Matthew D. Holcomb, Lebanon, OH (US); Michael J. Stokes, Cincinnati, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 321 days.

(21) Appl. No.: 14/239,899

(22) PCT Filed: Aug. 23, 2012

(86) PCT No.: PCT/US2012/052021
§ 371 (c)(1),
(2), (4) Date: Feb. 20, 2014

(87) PCT Pub. No.: WO2013/028841
PCT Pub. Date: Feb. 28, 2013

(65) Prior Publication Data
US 2014/0180192 A1 Jun. 26, 2014

(30) Foreign Application Priority Data
Aug. 23, 2011 (EP) .................................. 11178480

(51) Int. Cl.
*A61M 5/00* (2006.01)
*A61F 5/00* (2006.01)

(52) U.S. Cl.
CPC ........... *A61F 5/0076* (2013.01); *A61F 5/0089* (2013.01)

(58) Field of Classification Search
CPC .......... A61F 5/0076; A61F 2/04; A61F 2/24; A61F 5/0079; A61F 5/0083; A61F 2002/044; A61F 2220/0008; A61M 27/002; A61B 17/1114; A61B 17/221
USPC .............................. 604/8–10; 623/23.64–23.7
See application file for complete search history.

(56) References Cited

U.S. PATENT DOCUMENTS

| | | | |
|---|---|---|---|
| 7,121,283 | B2 | 10/2006 | Stack et al. |
| 7,267,694 | B2 | 9/2007 | Levine et al. |

(Continued)

FOREIGN PATENT DOCUMENTS

| | | |
|---|---|---|
| EP | 2298250 | 3/2011 |
| WO | WO 2012/007048 | 1/2012 |

OTHER PUBLICATIONS

Extended European Search Report re: 11178480.7 dated Jul. 3, 2012.

(Continued)

*Primary Examiner* — Philip R Wiest

(57) ABSTRACT

Endoluminal sleeve device (1) for internally lining a section of the GI tract, comprising a sleeve (2) configured for deployment inside a GI tract, the sleeve (2) having walls of a flexible material defining a sleeve lumen (3), a proximal end (4) defining a proximal lumen opening (5), and a distal end (6) defining a distal lumen opening (7), a tubular anchoring portion (8) forming said proximal lumen end (4) and defining anchoring seats (9) delimited each one by an annular collar (11) forming an opening through which adjacent tissue portions (12) can be pulled into the anchoring seats (9), expansion means adapted to act on the tissue portions (12) arranged in the anchoring seats (9) such that the tissue portions (12) expand to a dimension greater than the opening of the annular collar (11).

20 Claims, 2 Drawing Sheets

(56) References Cited

U.S. PATENT DOCUMENTS

2004/0148034 A1 7/2004 Kagan et al.
2004/0172141 A1 9/2004 Stack et al.
2005/0049718 A1 3/2005 Dunn et al.

OTHER PUBLICATIONS

International Search Report re: PCT/US2012/052021 dated Oct. 24, 2012.
International Preliminary Report on Patentability re: PCT/US2012/052021 dated Feb. 25, 2014.

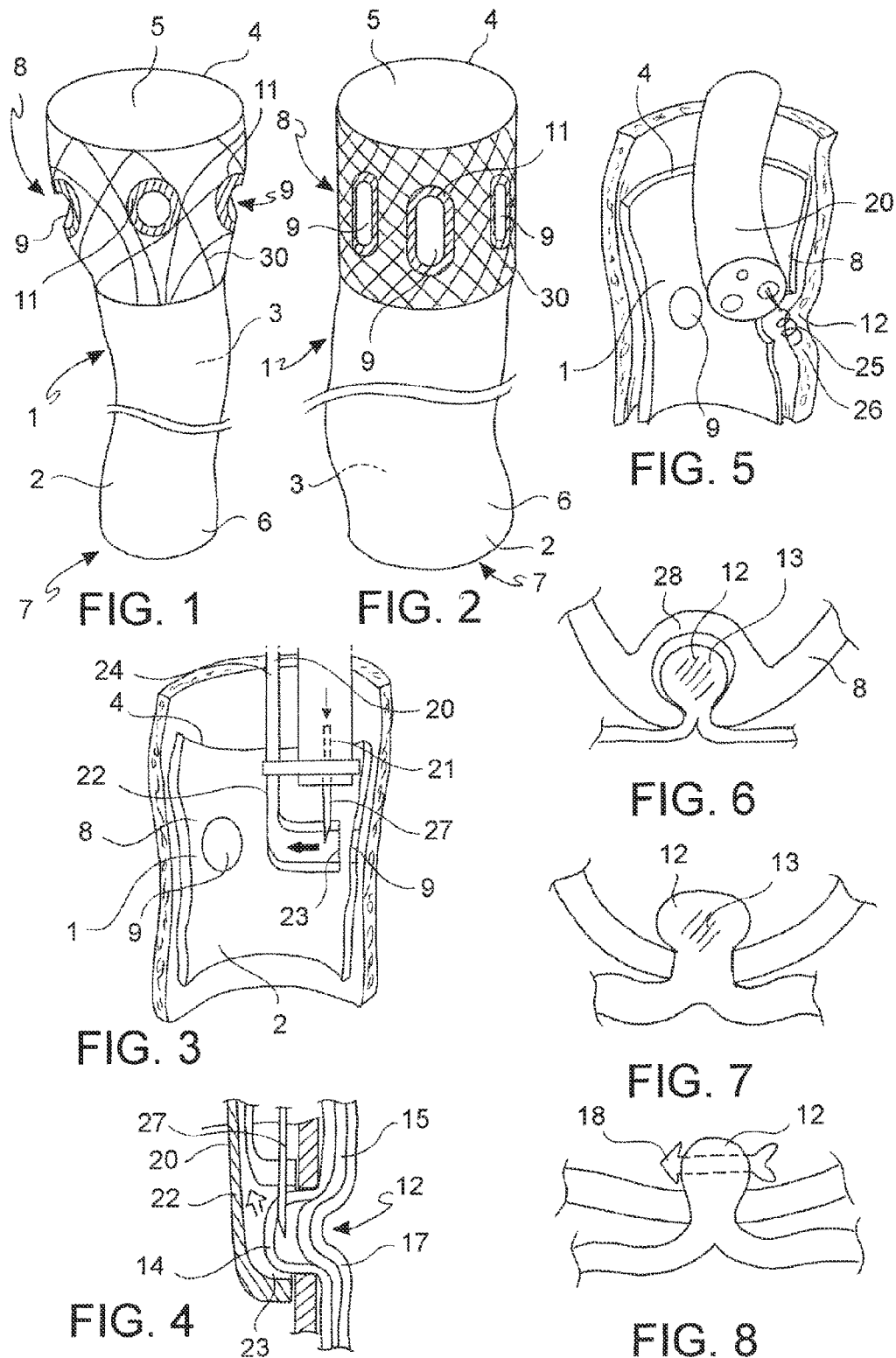

DEVICE FOR ANCHORING AN ENDOLUMINAL SLEEVE IN THE GI TRACT

FIELD OF THE INVENTION

The present invention relates generally to medical apparatuses and methods and more particularly to devices and methods for positioning and anchoring a lining to a hollow body organ, such as a stomach, intestine or gastrointestinal tract.

BACKGROUND OF THE INVENTION

In cases of severe obesity, patients may currently undergo several types of surgery either to tie off or staple portions of the large or small intestine or stomach, and/or to bypass portions of the same to reduce the amount of food desired by the patient, and the amount absorbed by the gastrointestinal tract. The procedures currently available include laparoscopic banding, where a device is used to "tie off" or constrict a portion of the stomach, vertical banded gastroplasty (VBG), or a more invasive surgical procedure known as a Roux-En-Y gastric bypass to effect permanent surgical reduction of the stomach's volume and subsequent bypass of the intestine.

Although the outcome of these stomach reduction surgeries leads to patient weight loss because patients are physically forced to eat less due to the reduced size of their stomach, several limitations exist due to the invasiveness of the procedures, including time, general anesthesia, healing of the incisions and other complications attendant to major surgery. In addition, these procedures are only available to severely obese patients (morbid obesity, Body Mass Index >=40) due to their complications, including the risk of death, leaving patients who are considered obese or moderately obese with few, if any, interventional options.

In addition to the above described gastrointestinal reduction surgery, endoluminal sleeves are known for partially or totally lining certain portions of the stomach and of the intestine with the aim to separate or bypass at least part of the food flow from the lined portions of the gastrointestinal tract. It has been observed that by creating a physical barrier between the ingested food and certain regions of the gastrointestinal wall by means of endoluminal sleeves, similar benefits for weight loss and improvement or resolution of type 2 diabetes may be achieved as with gastric bypass surgery. Physicians believe that by creating a physical barrier between the ingested food and selected regions of the gastrointestinal wall, it might be possible to purposefully influence the mechanism of hormonal signal activation originating from the intestine. It was observed that endoluminal sleeves in certain regions of the stomach and the duodenum contributed to improve glycemic control and to reduce or eliminate other co-morbidities of obesity. Moreover the lining of parts of the GI-tract by means of endosleeves provide an alternative or an additional therapy to traditional therapies of type II diabetes and obesity. Endosleeves may be placed in a brief and less invasive procedure and address the patient's fear of surgery. Contrary to traditional gastric bypass surgery, the result of endoluminal sleeve surgery is reversible and the sleeve can be removed after achievement of the clinical result, but also in case of the occurrence of undesired side effects or clinical complications. A typical duodenal sleeve device is described in U.S. Pat. No. 7,267,694 where the proximal end of a flexible, floppy sleeve of impermeable material defining a sleeve lumen is endoscopically deployed and anchored with the help of a barbed stent in the pylorus or in the superior section of the duodenum, the stent also ensuring that the proximal lumen opening of the sleeve remains open. Chyme from the stomach enters the proximal lumen opening of the sleeve and passes through the sleeve lumen to the distal lumen opening. Digestive enzymes secreted in the duodenum pass through the duodenum on the outside of the sleeve. The enzymes and the chyme do not mix until the chyme exits from the distal lumen opening of the liner tube. In such a way, the efficiency of the process of digestion of the chyme is diminished, reducing the ability of the gastrointestinal tract to absorb calories from the food.

G.I. Dynamics, Inc., (Watertown, Mass., USA) produces the Endobarrier(R) device that is substantially a duodenal sleeve device configured so that the proximal end of the device is anchored inside the duodenal bulb with the help of a barbed anchoring stent that also keeps the proximal lumen opening open.

In U.S. 2004/0148034 is taught a duodenal sleeve device attached to a funnel, the funnel configured for anchored to the gastric walls inside the gastric cavity in proximity to the lower esophageal sphincter. Food passing the lower esophageal sphincter is directed by the funnel into the proximal lumen opening of the duodenal sleeve device.

In U.S. Pat. No. 7,121,283 is taught a duodenal sleeve device attached to a large stent-like anchoring device that presses outwardly against the pyloric portion of the stomach, the pyloric sphincter and the duodenal bulb.

In known endosleeves, it has been observed that the sleeve devices tend to move inside the GI tract and migrate away from their original anchoring position.

A further important issue with endoluminal sleeves is the risk of failure of sealing of the lined lumen and, hence, the risk of an undesired leakage of the partially digested food flow in the interstice between the lumen wall and the sleeve. Moreover, known endoluminal sleeve attachment devices and methods are not yet fully satisfying with regard to permitting normal biological events, including vomiting, to occur.

Further fields of desirable improvements related with endoluminal sleeves are their removal from the patient without injuring the involved tissues, the rapidity of deployment and removal of the sleeve, and the repeatability of the sleeve placement.

Accordingly, there is a need for improved devices and procedures for anchoring and sealing an endoluminal, particularly a duodenal sleeve in the GI tract.

SUMMARY OF THE INVENTION

The present invention provides for an endoluminal, particularly duodenal, sleeve device and method for the transoral, or endoscopic, positioning and anchoring of an endoluminal sleeve device within a gastrointestinal tract, including, but not limited to, the pylorus, the esophagus, stomach, duodenum as well as other portions of or the entire length of the intestinal tract, etc., unless specified otherwise. In the case of the present invention, the surgeon or endoscopist may insert devices as described below through the patient's mouth, down the esophagus and into the stomach or intestine as appropriate. The procedure can be performed entirely from within the patient's stomach or other intestinal tract, and does not necessarily require any external incision. Alternatively, the surgeon may insert devices as described below laparoscopically into the stomach or intestine as appropriate.

According to an aspect of the invention, there is provided a duodenal sleeve device, comprising:

a sleeve configured for deployment inside a duodenum of a human subject, the sleeve having walls of a flexible material defining a sleeve lumen, a proximal end defining a proximal lumen opening, and a distal end defining a distal lumen opening, a tubular anchoring portion forming the proximal lumen end and having a plurality of anchoring seats delimited by an annular collar defining an opening through which adjacent tissue portions can be pulled into the anchoring seats, expansion means adapted to act on the tissue portions arranged in the anchoring seats such that the tissue portions expand to a dimension greater than the opening of the annular collar.

This provides a direct shape lock between the proximal sleeve end and the surrounding tissue which eliminates the risk of undesired migrating of the proximal lumen opening away from its planned position.

In accordance with an aspect of the invention, the expansion means may comprise an expansion promoter which can be injected or implanted into the tissue portion trapped in the anchoring seat.

In accordance with a further aspect of the invention, the annular collar of the anchoring seat is configured to controllably constrict, thereby further improving the shape lock of the tissue portion trapped inside the anchoring seat.

In accordance with a further aspect of the invention, the tubular anchoring portion comprises elastic means which bias the anchoring seats 9 permanently radially outward. Such an elastic preload contributes to holding the anchoring portion in permanent contact with the surrounding gastrointestinal tissue which is constantly moving due to peristalsis. Thus, a reliable sealing against leakage is achieved, as well as a firm placement of the anchoring seats over the entrapped tissue portions. In accordance with a yet further aspect of the invention, the anchoring portion is formed substantially by a wire mesh stent or comprises a wire mesh stent and the anchoring seats are provided in holes in the stent which have a size adapted to allow that externally surrounding tissue be pulled therethrough to an internal side of the stent.

These and other aspects and advantages of the present invention shall be made apparent from the accompanying drawings and the description thereof, which illustrate embodiments of the invention and, together with the general description of the invention given above, and the detailed description of the embodiments given below, serve to explain the principles of the present invention.

BRIEF DESCRIPTION OF THE DRAWINGS

FIG. 1 illustrates a duodenal sleeve device in accordance with an embodiment;

FIG. 2 illustrates a duodenal sleeve device in accordance with a further embodiment;

FIG. 3 illustrates a duodenal sleeve device in a partial longitudinal cross-section during anchoring thereof within the GI tract;

FIG. 4 illustrates a method step of anchoring the duodenal sleeve device in the GI tract in accordance with an embodiment;

FIG. 5 illustrates a method step of anchoring the duodenal sleeve device in the GI tract in accordance with a further embodiment;

FIGS. 6, 7 and 8 are cross-sectional views of anchoring regions between tissue of the GI tract and the duodenal sleeve device in accordance with embodiments;

DETAILED DESCRIPTION OF EMBODIMENTS

Figures 9, 10:
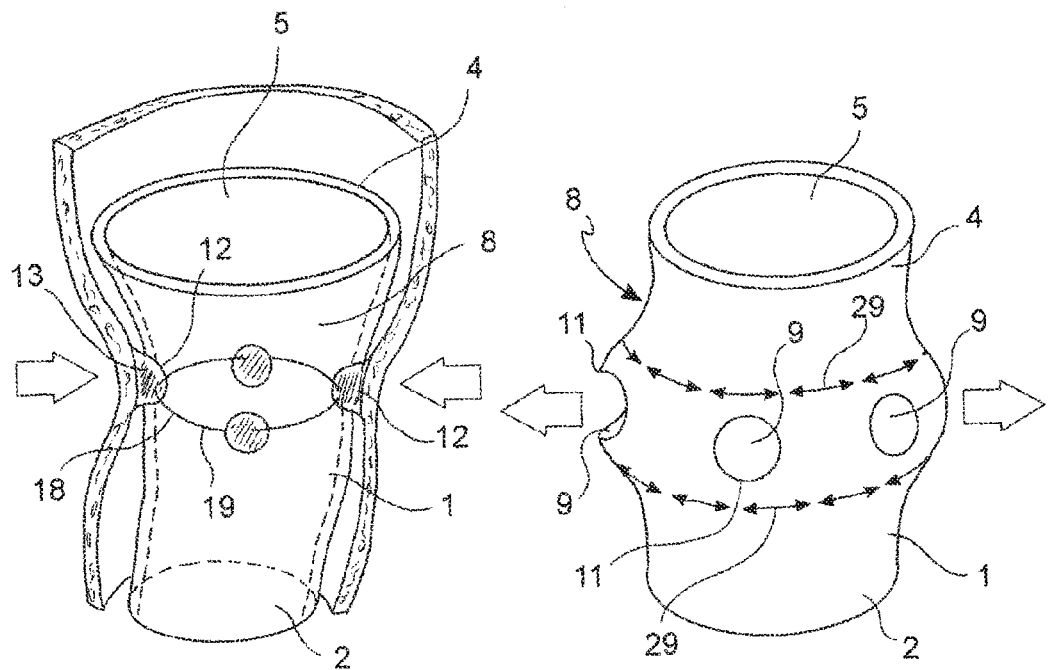
FIG. 9 illustrates a further method step of anchoring the duodenal sleeve device in the GI tract, in accordance with an embodiment.
FIG. 10 illustrates an elastically biased anchoring portion of the sleeve device in accordance with an embodiment.
Figure 11:
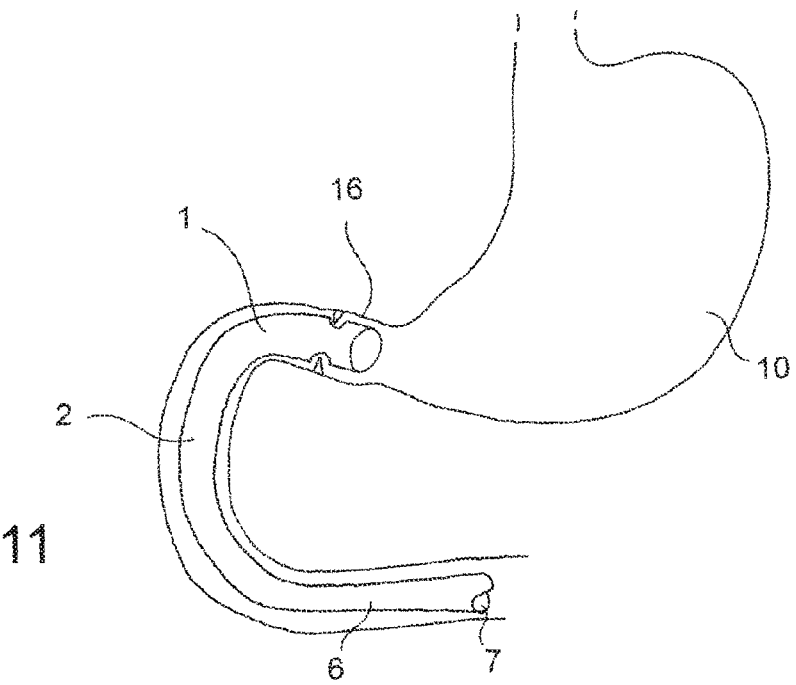
FIG. 11 illustrates the duodenal sleeve device after anchoring thereof inside the GI tract.

Referring to the drawings where like numerals denote like anatomical structures and components throughout the several views, an endoluminal sleeve device 1 for internally lining a section of the GI tract, particularly a section of duodenum distally from the pylorus, comprises a sleeve 2 configured for deployment inside a duodenum of a human subject, the sleeve 2 having walls of a flexible material defining a sleeve lumen 3, a proximal end 4 defining a proximal lumen opening 5, and a distal end 6 defining a distal lumen opening 7. The device 1 comprises further a tubular anchoring portion 8 which forms the proximal lumen end 4 and which has a plurality of anchoring seats 9 delimited by an annular collar 11 forming an opening through which adjacent tissue portions 12 can be pulled into the anchoring seats 9. The device 1 comprises further expansion means adapted to act on the tissue portions 12 arranged in the anchoring seats 9 such that the tissue portions 12 expand to a dimension greater than the opening of the annular collar 11.

This provides a direct shape lock between the proximal sleeve end and the surrounding tissue which eliminates the risk of undesired migrating of the proximal lumen opening away from its planned position.

In accordance with an embodiment, the expansion means may comprise an expansion promoter 13 which can be injected or implanted into the tissue portion 12 trapped in the anchoring seat 9, such as a swelling agent or sclerosant agent or a plastic bead insert of e.g. Poly(methyl methacrylate) PMMA. Preferably, as illustrated in FIG. 4, the expansion promoter 13 is applied in or near the interface region between the mucosa 14 and the submucosa 15 in order to not influence the muscularis layer 17 of the gastric or intestinal wall.

In accordance with a further embodiment, after the tissue portions 12 are placed within the anchoring seats 9, they can be additionally secured by inserting at least one mechanical latch member 18 through the tissue portions 12 such that two opposite end portions of the mechanical latch member 18 protrude out of the tissue portion 12 and overlap with the annular collar 11 from an internal side of the anchoring portion 8. The mechanical latch members 18 may comprise e.g. piercing rods, rings, sutures or surgical buttress and can be deployed while the not yet expanded tissue portions are held inside the anchoring seats 9 or after expanding the tissue portions 12. The mechanical latch members 18 can be connected to each other (e.g. by a suture loop) or can form a closed loop 19, e.g. a suture loop, which loop 19 can be tightened in a purse string fashion to restrict the anchoring region, if required, and to assure a substantially constant anchoring and sealing perimeter and proximal lumen opening.

In accordance with an embodiment, a complete surgical kit can be provided which contains the sleeve device 1, a tissue acquisition device 20 (FIGS. 3, 4, 5) adapted and operable to acquire the surrounding tissue from inside the anchoring portion 8 through the collar 11 and to pull the acquired tissue into the anchoring seat 9. Additionally, an injection device 21 may be provided which is adapted and operable to pierce the tissue portion 12 trapped inside the anchoring seat 9 and to inject or push the expansion promoter 13 into the tissue portion 12.

In accordance with an embodiment (FIGS. 3, 4), the tissue acquisition device can comprise an endoluminal suction device 22 having a suction opening 23 oriented transversally to a longitudinal (proximal-distal) extension of the device and which suction opening 23 can be arranged in fluid communication with the anchoring seat 9. The suction opening 23 is connected by a suction line 24 to an extracorporeal vacuum source (not shown) in order that vacuum can be applied through the anchoring seat 9 to externally adjacent tissue, which is hence pulled into the anchoring seat 9.

In accordance with a further embodiment (FIG. 5), the tissue acquisition device 20 can comprise an endoluminal grasping device 25 having a grasper or corkscrew piercer 26 which is orientable transversally to a longitudinal (proximal-distal) extension of the device and which can be moved from inside the anchoring seat 9 through the collar 11 to the externally adjacent tissue in order to grasp it and pull it into the anchoring seat 9.

In accordance with a further embodiment, the injection device 21 may comprise a hollow tubular injection needle 27 which is supported and guided by the tissue acquisition device 20 and operable to inject the expansion promoter 13 while the tissue acquisition device 20 is applying a pulling force on the tissue portion 12 trapped in the anchoring seat 9.

In accordance with an embodiment (FIGS. 3 and 4), the injection needle 27 is operable to be pushed into an internal lumen of the suction opening 23 of the suction device 22. In a further embodiment (FIG. 5), the hollow tubular injection needle 27 can be directly formed by the corkscrew shaped piercer 26 of the grasping device 25 or, alternatively by one of two opposing jaws of a grasper (not shown).

In accordance with a further embodiment, the annular collar 11 of the anchoring seat 9 is configured to controllably constrict, thereby further improving the shape lock of the tissue portion 12 inside the anchoring seat 9.

For this purpose, the collar 11 may comprise heat shrinkable material, shape memory material or phase changeable material which, in response to thermal activation (e.g. heating), constricts the collar lumen.

In accordance with a further embodiment, the anchoring seat 9 is at least partially defined by a heat shrinkable membrane 28 adapted to forcefully collapse over the tissue portion 12 trapped in the anchoring seat 9 in response to thermal activation, e.g. heating of the membrane 28.

In accordance with a further embodiment, the tubular anchoring portion 8 comprises elastic means 29 which bias the anchoring seats 9 permanently radially outward. Such an elastic preload contributes to holding the anchoring portion 8 in permanent contact with the surrounding gastro-intestinal tissue which is constantly moving due to peristalsis. Thus, a reliable sealing against leakage of food and chyme into the interstice between the sleeve and the intestinal wall is achieved, as well as a firm placement of the anchoring seats 9 over the entrapped tissue portions 12.

In accordance with embodiments, the elastic means 29 may comprise e.g. an elastomeric cylindrical body or a series of elastic spring rings connected to or encapsulated in the tubular wall of the anchoring portion 8.

The anchoring seats 9 are preferably arranged at a constant angular pitch along one or more circumferential rows. The anchoring seats 9 of adjacent rows may be staggered to improve overall sealing of the proximal sleeve end 4 against the gastro-intestinal wall. A preferred number of anchoring seats 9 formed in a circumferential row ranges from 2 to 4 seats.

In accordance with an embodiment, the anchoring portion 8 may be formed substantially by a wire mesh stent 30 or comprises a wire mesh stent 30 and the anchoring seats 9 are delimited by holes in the stent which have a size adapted to allow that externally surrounding tissue be pulled therethrough to an internal side of the stent 30.

The sleeve device 1 may be placed in numerous locations in the GI tract, particularly in the duodenum, distal antrum of the stomach 10 and the distal esophagus.

In accordance with an alternative method, plications or similarly bulky protrusions are created in the stomach and the sleeve anchoring portion 8 is configured that the anchoring seats 9 may receive the previously created protrusions to lock the sleeve device 1 in the GI tract. In this case it is not necessary but possible to subsequently expand the trapped protrusions.

The protrusions can be formed e.g. by endoluminally stapling the gastro-intestinal wall, thereby creating one or more ridges within the GI tract. Additionally or alternatively, mechanical fasteners, e.g. T-tags, pledgets, expandable baskets, H-fasteners, can be driven in the tissue portions or permanently attached thereto in order to create gastric wall plications or intestinal wall plications.

The sleeve anchoring portion 8 with anchoring seats 9 shaped to accommodate these ridges is then positioned to mate with the protrusions. As described above, a mechanical latch member 18 can be pierced through the tissue protrusion (and in some embodiments also through a wall of the anchoring seat) to secure the sleeve device 1 in place.

In accordance with a further embodiment, the anchoring portion of the sleeve device may form a higher number of anchoring seats 9 than the number of tissue wall protrusions in order to increase the probability that at least one or more protrusions are caught in the anchoring seats 9.

The sleeve 2 itself is sufficiently flexible to follow the curvature of the duodenum. Further, in some embodiments the walls of the sleeve are sufficiently flexible and/or collapsible to allow duodenal peristalsis to drive chyme through the lumen of the sleeve. Sufficient collapsibility of the walls of the sleeve prevents continuous intimate contact of the outer surface of the sleeve with the duodenal mucosa, avoiding damage to the duodenal mucosa and allowing digestive secretions not collected into the sleeve lumen to pass through the duodenal lumen outside the sleeve lumen.

In some embodiments, at least a portion of the wall of a sleeve may be porous or semipermeable to allow entry of digestive secretions into the sleeve lumen and/or to allow the flow of fluids and digested matter out of the sleeve lumen.

In some embodiments, at least a portion of the wall of a sleeve may be impermeable, analogous to the Endobarrier (R) by GI Dynamics Inc, Watertown, Mass., USA and as described in U.S. Pat. No. 7,267,694 which is included by reference as if fully set forth herein.

The diameter of the sleeve lumen may be substantially constant along the entire length of the liner tube. Although any suitable luminal diameter may be used, in some embodiments, the luminal diameter may be not more than about 30 mm, not more than about 25 mm and even not more than about 20 mm.

In some embodiments, the proximal end of the sleeve may be flared and may define a funnel-like structure.

The length of the sleeve may be any suitable length and may be selected in accordance with clinical decisions made by the treating physician. A typical sleeve is between about 25 cm and about 160 cm long. Generally, the sleeve is selected so that when the duodenal sleeve device is deployed, the distal lumen opening of the sleeve is located distal to the duodenal-jejunal flexure and empties out into the jejunum. In some embodiments, the sleeve may be even longer.

Suitable materials from which the sleeve for implementing the invention are fashioned include silicone, polyurethane, polyethylene (e.g., low density polyethylene films) and fluoropolymers (e.g., expanded polytetrafluoroethylene) . In some embodiments, the sleeve is fashioned from fluoropolymer or polyethylene film impregnated with polyurethane or silicone to reduce permeability, as taught in U.S. Pat. No. 7,267,694.

The sleeve may include one or more markers (e.g., barium) designed for viewing the position of the sleeve within the intestines through fluoroscopy, such as a longitudinal rib or other markers that are spaced along the length of sleeve. In addition, sleeve may further include components that inhibit twisting or kinking of the sleeve itself. In one embodiment, these components include one or more stiffening elements, such as rings, coupled to either the inside or the outside of the sleeve at spaced locations along its length. These rings can, for example, be made of a slightly thicker silicone material that would resist twisting or kinking of the sleeve around the ring. In other embodiments, the stiffening elements may be in spiral shape or extending lengthwise along at least a portion of the sleeve.

In an implantation method, the sleeve may be initially folded or rolled up and packed into the interior of an applier. The distal end of sleeve may be initially closed, e.g. with a small polymeric or silicone seal and forms a programmed tearing line, e.g. a perforation, along which the distal end can tear open by the internal pressure of the chyme flow.

In this way bypass conduits can be created in the GI tract of a patient to achieve a malabsorptive effect in cases where such an effect may enhance weight loss, as well as the initially described effects on hormonal signaling in general.

Particularly, the described devices and procedures obviate undesired migration of the sleeve away from its original anchoring position and addresses the need of reliable sealing of the lined lumen. Moreover, some embodiments of the described devices and methods are beneficial with regard to permitting normal biological events, including vomiting, to occur.

Although preferred embodiments of the invention have been described in detail, it is not the intention of the applicant to limit the scope of the claims to such particular embodiments, but to cover all modifications and alternative constructions falling within the scope of the invention.

The invention claimed is:

1. Endoluminal sleeve device (1) for internally lining a section of the GI tract, comprising: a sleeve (2) configured for deployment inside a GI tract, the sleeve (2) having walls of a flexible material defining a sleeve lumen (3), a proximal end (4) defining a proximal lumen opening (5), and a distal end (6) defining a distal lumen opening (7), a tubular anchoring portion (8) forming said proximal lumen end (4) and defining anchoring seats (9) delimited by an annular collar (11) forming an opening through which adjacent tissue portions (12) can be pulled into the anchoring seats (9), expansion means adapted to act on the tissue portions (12) arranged in the anchoring seats (9) such that the tissue portions (12) expand to a dimension greater than the opening of the annular collar (11).

2. Endoluminal sleeve device (1) according to claim 1, in which the annular collar (11) is activatable to controllably constrict.

3. Endoluminal sleeve device (1) according to claim 2, in which the collar (11) comprise one of: heat shrinkable material, shape memory material, phase changeable material, which, in response to thermal activation constricts the collar (11) opening.

4. Endoluminal sleeve device (1) according to claim 1 or 2, in which the anchoring seat (9) is at least partially defined by a heat shrinkable membrane (28) adapted to collapse over the tissue portion (12) trapped in the anchoring seat (9) in response to thermal activation.

5. Endoluminal sleeve device (1) according to claim 1 or 2 in which the tubular anchoring portion (8) comprises elastic means (29) which bias the anchoring seats (9) permanently radially outward.

6. Endoluminal sleeve device (1) according to claim 1 or 2, in which the expansion means comprise one of an injectable swelling agent, sclerosant agent, plastic bead insert.

7. Endoluminal sleeve device (1) according to claim 1 or 2, comprising a plurality of mechanical latch members (18) which can be pierced through the tissue portions (12) trapped in the anchoring seats (9) and which have a shape such that two opposite end portions of the mechanical latch member (18) can protrude out of the tissue portion (12) and overlap with the annular collar (11) from an internal side of the anchoring portion (8).

8. Endoluminal sleeve device (1) according to claim 7, in which all mechanical latch members (18) are connectable to each other to form a closed loop (19).

9. Endoluminal sleeve device (1) according to claim 1 or 2, in which said anchoring seats (9) are preferably arranged at a constant angular pitch along at least one circumferential row.

10. Endoluminal sleeve device (1) according to claim 6, in which the anchoring seats (9) of adjacent rows are staggered.

11. Surgical instrumentation kit for internally lining a section of GI tract, including: the sleeve device (1) according to claim 1 or 2, a tissue acquisition device (20) adapted and operable to acquire the surrounding tissue from inside the anchoring portion (8) of the sleeve device (1) through the collar (11) into the anchoring seat (9), an injection device (21) adapted and operable to pierce the tissue portion (12) trapped inside the anchoring seat (9) and to inject the expansion means (13) into the tissue portion (12).

12. Surgical instrumentation kit according to claim 11, in which the injection device (21) comprises a hollow tubular injection needle (27) supported and guided by the tissue acquisition device (20) and operable to inject the expansion promoter (13) while the tissue acquisition device (20) is applying a pulling force on the tissue portion (12) trapped in the anchoring seat (9).

13. Surgical instrumentation kit according to claim 12, in which the injection needle (27) is directly formed by a corkscrew shaped piercer (26) of the tissue acquisition device (20).

14. Method for internally lining a section of the GI tract, comprising: providing a sleeve device (1) with: a) a sleeve (2) having walls of a flexible material defining a sleeve lumen (3), a proximal end (4) defining a proximal lumen opening (5), and a distal end (6) defining a distal lumen opening (7), b) a tubular anchoring portion (8) forming said proximal lumen end (4) and defining anchoring seats (9) delimited by an annular collar (11), inserting the sleeve device (1) in the GI tract, pulling adjacent gastrointestinal tissue through the collars (11) into the anchoring seats (9), expanding the tissue portions (12) pulled in the anchoring seats (9) to a dimension greater than the opening of the annular collar (11).

15. Method according to claim 14, in which the step of expanding the tissue portions (12) comprises injecting an expansion promoter into the tissue portion (12) while holding it the anchoring seat (9).

16. Method according to claim 14, in which the expansion promoter (13) is introduced near the interface region between a mucosa (14) and a submucosa (15) of the gastrointestinal wall.

17. Method according to claim 14, comprising inserting at least one mechanical latch member (18) through the tissue portions (12) such that two opposite end portions of the mechanical latch member (18) protrude out of the tissue portion (12) and overlap with the annular collar (11) from an internal side of the anchoring portion (8).

18. Method according to claim 17, comprising connecting the mechanical latch members (18) to each other to form a closed loop (19).

19. Method according to claim 18, comprising tightening the closed loop (19) in a purse string fashion to restrict the anchoring region.

20. Method according to claim 14, comprising constricting the annular collar (11).

\* \* \* \* \*